United States Patent
Liu et al.

(10) Patent No.: US 10,460,828 B2
(45) Date of Patent: Oct. 29, 2019

(54) METHOD OF NUCLEIC ACID FRAGMENT DETECTION

(71) Applicant: LifeOS Genomics Corporation, Grand Cayman (KY)

(72) Inventors: Timothy Z. Liu, Fremont, CA (US); Ching-Jou Huang, Taichung (TW)

(73) Assignee: Lifeos Genomics Corporation, Grand Cayman (KY)

( * ) Notice: Subject to any disclaimer, the term of this patent is extended or adjusted under 35 U.S.C. 154(b) by 0 days.

(21) Appl. No.: 15/714,401

(22) Filed: Sep. 25, 2017

(65) Prior Publication Data

US 2018/0096098 A1    Apr. 5, 2018

Related U.S. Application Data

(60) Provisional application No. 62/401,893, filed on Sep. 30, 2016.

(51) Int. Cl.
| | | |
|---|---|---|
| C12Q 1/68 | (2018.01) | |
| G16B 25/00 | (2019.01) | |
| G16B 40/00 | (2019.01) | |
| C12Q 1/6816 | (2018.01) | |
| G01N 33/50 | (2006.01) | |
| C12Q 1/682 | (2018.01) | |

(52) U.S. Cl.
CPC .............. *G16B 25/00* (2019.02); *C12Q 1/682* (2013.01); *C12Q 1/6816* (2013.01); *G01N 33/50* (2013.01); *G16B 40/00* (2019.02)

(58) Field of Classification Search
None
See application file for complete search history.

(56) References Cited

U.S. PATENT DOCUMENTS

2006/0275782 A1* 12/2006 Gunderson .......... C12Q 1/6837
435/6.12
2016/0130653 A1    5/2016 Ho et al.

FOREIGN PATENT DOCUMENTS

WO    2013130674 A    9/2013

OTHER PUBLICATIONS

Degliangeli, Federica, et al., "Absolute and Direct MrcroRNA Quantification Using DNA-Gold Nanoparticle Probes", Journal of the American Chemical Society, published on Feb. 12, 2014, pp. 2264-2267, vol. 136, No. 6, American Chemical Society, U.S.A.
Dong, Haifeng, et al., "Highly Sensitive and Selective MicroRNA Detection Based on DNA-Bio-Bar-Code and Enzyme-Assisted Strand Cycle Exponential Signal Amplification", Analytical Chemistry, published on Apr. 1, 2015, pp. 4334-4340, vol. 87, No. 8, American Chemical Society, U.S.A.
Lv, Weifeng, et al., "A target-triggered dual amplification strategy for sensitive detection of microRNA", Biosensors and Bioelectronics, published on Sep. 15, 2016, pp. 250-255, vol. 83, Elsevier B.V., Netherlands.
Tian, Tian, et al., "A review: microRNA detection methods", Organic & Biomolecular Chemistry, published on Feb. 28, 2015, pp. 2226-2238, Issue 8, Royal Society of Chemistry, United Kingdom.
Zhang, Kai, et al., "Sensitive detection of microRNA in complex biological samples by using two stages DSN-assisted target recycling signal amplification method", Biosensors and Bioelectronics, published on Jan. 15, 2017, pp. 358-364, vol. 87, Elsevier B.V., Netherlands.

* cited by examiner

*Primary Examiner* — James Martinell

(57) ABSTRACT

A method of nucleic acid fragment detection includes capturing a target nucleic acid fragment by an oligonucleotide probe to form a hybridised double strand. The oligonucleotide probe has an identification sequence complementary to the target nucleic acid fragment and a reproducible sequence. The hybridised double strand is removed to expose the reproducible sequence of the oligonucleotide probe. The repeats of the reproducible sequence are produced. The repeats of the reproducible sequence are labelled by a detection probe for identification and quantitation.

14 Claims, 17 Drawing Sheets

METHOD OF NUCLEIC ACID FRAGMENT DETECTION

RELATED APPLICATIONS

This application claims priority to U.S. Provisional Application Ser. No. 62/401,893, filed Sep. 30, 2016, which is herein incorporated by reference in its entirety.

BACKGROUND

Field of Invention

The present invention relates to nucleic acid fragment detection method. More particularly, the present invention relates to a detection method of nucleic acid fragment detection with telomerase extension or polymerase replication.

Description of Related Art

MicroRNAs (miRNAs) are short ribonucleic acid (RNA) molecules, consisting of 21-25 nucleotide bases. There have been many studies of miRNA regulation implicated in the etiology and progression of diseases, such as cancer, heart disease, and Parkinson disease. In addition, circulating miRNAs show great influence as a regulator in biological functions. The regulatory function of miRNAs affects cellular processes, such as proliferation or apoptosis, and correlation between miRNAs and cancer development is strong. Studies have shown that miRNAs are important biomarkers for different diseases. There is a strong need for a tool that can facilitate the analysis of the expression levels of the rapidly growing list of miRNA biomarkers that have been identified so far in the eukaryotic pool.

SUMMARY

In some embodiments, the instant disclosure provides a method of nucleic acid fragment detection. A target nucleic acid fragment is captured by an oligonucleotide probe to form a hybridised double strand. The oligonucleotide probe has an identification sequence complementary to the target nucleic acid fragment and a telomere sequence. The hybridised double strand is removed to expose the telomere sequence of the oligonucleotide probe. The repeats of the telomere sequence are produced. The repeats of the telomere sequence are labelled by detection probes.

In some embodiments, the oligonucleotide probe has an identification sequence complementary to the target nucleic acid fragment and a specific sequence that can serve as a primer for rolling circle amplification (RCA). The hybridised double strand is removed to expose the specific RCA primer sequence of the oligonucleotide probe. The repeats of the RCA sequence are produced via the extension of the said specific RCA primer sequence. The repeats of the RCA sequence are detected by detection probes. In some embodiments, the removal of the hybridised double strand includes cleaving the hybridized double strand off the oligonucleotide probe by duplex specific nuclease (DSN).

In some embodiments, the method includes identifying the target nucleic acid fragment according to a spatial resolution.

In some embodiments, the method includes providing a substrate having an immobile probe. The repeats of telomere sequence are captured through the immobile probe. The immobile probe has a sequence complementary to a segment of the oligonucleotide probe.

Due to the telomere repeats or RCA repeats, signal amplification is even more pronounced. Duplex-specific Nuclease (DSN) based enzymatic assay scheme identifies sequence of interest and exposes the reproducible sequence for extension and detection. This assay scheme is amenable to a fully automated process of nuclei acid fragment detection and quantitation. The target specific capture probes can be separately immobilized at different known locations on the substrate surface so as to obtain spatial resolution information. The signals from different locations on the substrate surface indicate the identity of different target nuclei acid fragments in the sample. In addition, the amount of target sequence can also be quantified.

The detection method can provide specific and sensitive multiplex detection of target fragment(s) from a variety of biological samples for use in biomedical research and clinical diagnostics applications.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
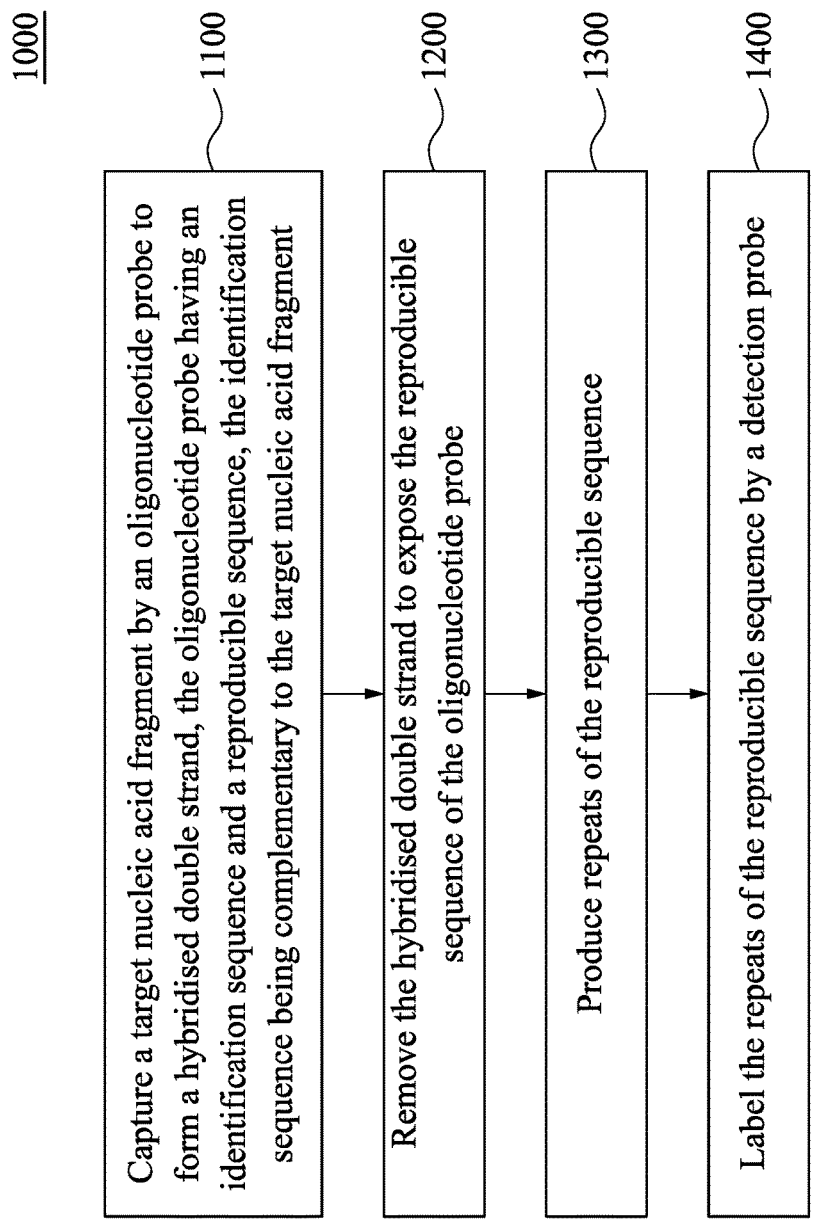
FIG. 1 is a flow chart illustrating a method of nucleic acid fragment detection in accordance with some embodiments of the instant disclosure.

Reference will now be made in detail to the present embodiments of the invention, examples of which are illustrated in the accompanying drawings. Wherever possible, the same reference numbers are used in the drawings and the description to refer to the same or like parts.

Reference is made to FIG. 1, illustrating a flow chart of a method 1000 of nucleic acid fragment detection method in accordance with some embodiments of the instant disclosure. The method begins with operation 1100 in which a target nucleic acid fragment is captured by an oligonucleotide probe to form a hybridised double strand. The oligonucleotide probe has an identification sequence and a reproducible sequence. The identification sequence is complementary to the target nucleic acid fragment. The method continues with operation 1200 in which the hybridised double strand is removed to expose the reproducible sequence of the oligonucleotide probe. Subsequently, operation 1300 is performed. Repeats of the reproducible sequence are produced. The method continues with operation 1400 in which the repeats of the reproducible sequence are labelled by a detection probe. The method proceeds to operation 1400 in which the signals from the detection probe is analysed, and the target nucleic acid fragments are quantified according to the detected signals. The said detection probes can be labelled with various chemical or physical moieties that generate detectable signals under appropriate conditions. These detectable labels are well known in the art, comprising quantum dots, fluorescent dyes, or electrochemical molecules. The discussion that follows illustrates embodiments of nucleic acid fragment detection method according to the method 1000 of FIG. 1. While method 1000 is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

FIGS. 2 through 9 illustrate various stages of a nucleic acid fragment detection method in accordance with some embodiments of the instant disclosure.

Figure 2:
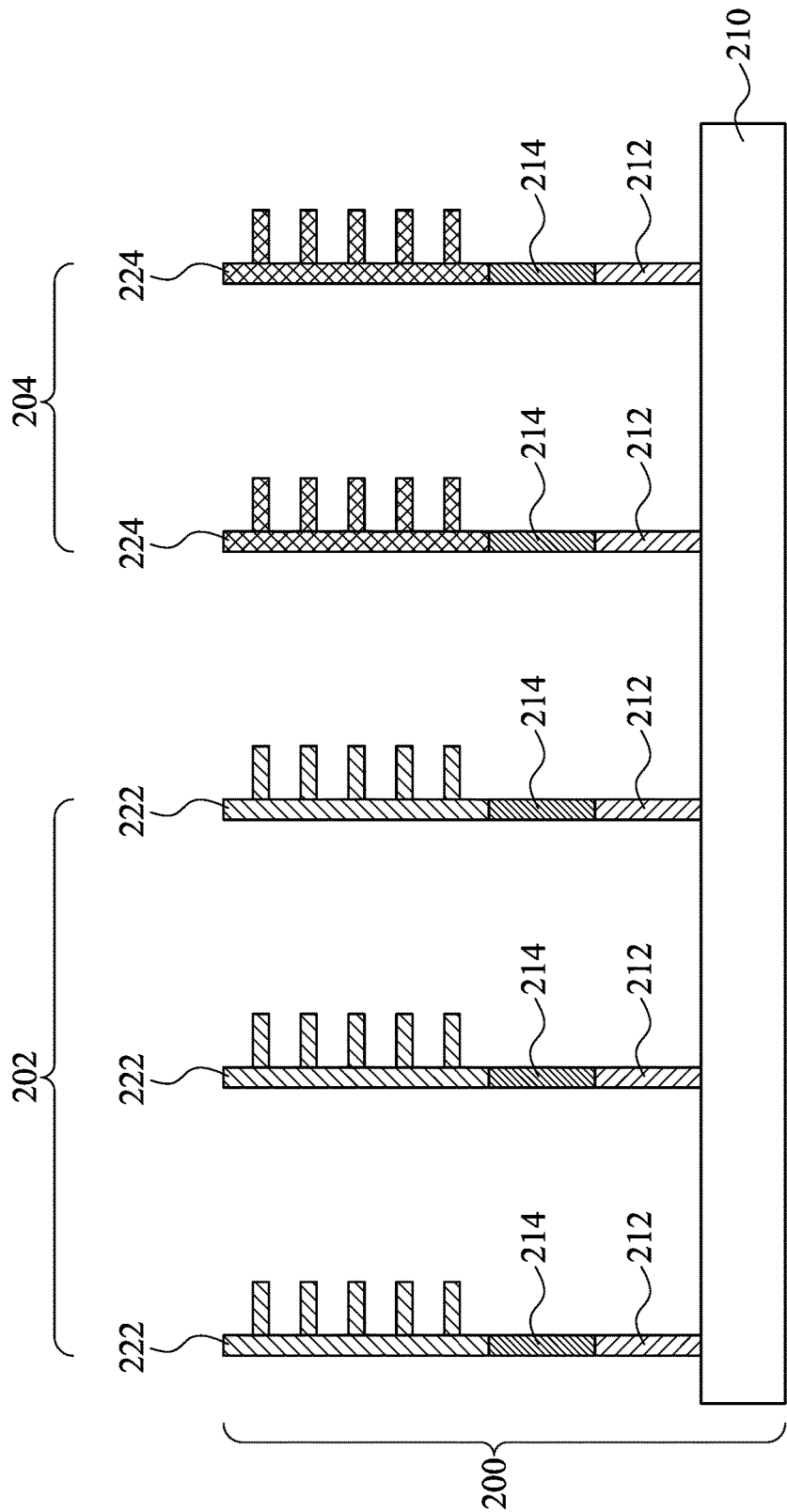
FIGS. 2 through 9 illustrate a method of nucleic acid fragment detection at various stages in accordance with some embodiments of the instant disclosure.

Reference is made to FIG. 2, illustrating a substrate having a plurality of oligonucleotide probes. The substrate 210 has a planar surface and bonded with a plurality of oligonucleotide probes 200. Examples of materials of the substrate 210 include but not limited to, polystyrene, Polydimethylsiloxane (PDMS), glass, silicon or gold. In some embodiments, each of the oligonucleotide probes 200 is single strand and has an immobilization anchor, a reproducible sequence, and an identification sequence. Based on different identification sequences, the oligonucleotide probes 200 may have different types of oligonucleotide probes. For example, as shown in FIG. 2, the oligonucleotide probes 200 include first oligonucleotide probes 202 and second oligonucleotide probes 204. Each of the first oligonucleotide probes 202 has the immobilization anchor 212, reproducible sequence 214, and a first identification sequence 222. The immobilization anchor 212 allows the first oligonucleotide probes 202 to be attached on the substrate 210 surface through covalent bonds, for example. The 3' end of the reproducible sequence 214 includes a telomerase recognition sequence. The first identification sequence 222 is attached to the 3' end of the telomere sequence 214. The first identification sequence 222 contains complementary sequence to a first type nucleic acid fragment and will attract the first type nucleic acid fragment binding.

Reference is still made to FIG. 2. Likewise, each of the second oligonucleotide probes 204 has the immobilization anchor 212, the reproducible sequence 214, and a second identification sequence 224. The immobilization anchor 212 and the reproducible sequence 214 are identical to the first oligonucleotide probes 202. In some embodiments, the reproducible sequence 214 is telomeres specific. That is, the reproducible sequence 214 allows telomerase recognition for amplification. The difference between the first oligonucleotide probes 202 and the second oligonucleotide probes 204 arises from the first identification sequence 222 and second identification sequence 224. The second identification sequence 224 is attached to the 3' end of the telomere sequence 214, and the second identification sequence 224 contains complementary sequence to a second type nucleic acid fragment. Because of different identification sequences, the first oligonucleotide probes 202 and the second oligonucleotide probes 204 attract different types of nucleic acid fragments. The number of oligonucleotide probes may vary according to detection requirement, and the types of oligonucleotide probes may be one, two, three or more, and the instant disclosure is not limited thereto.

Figure 3:
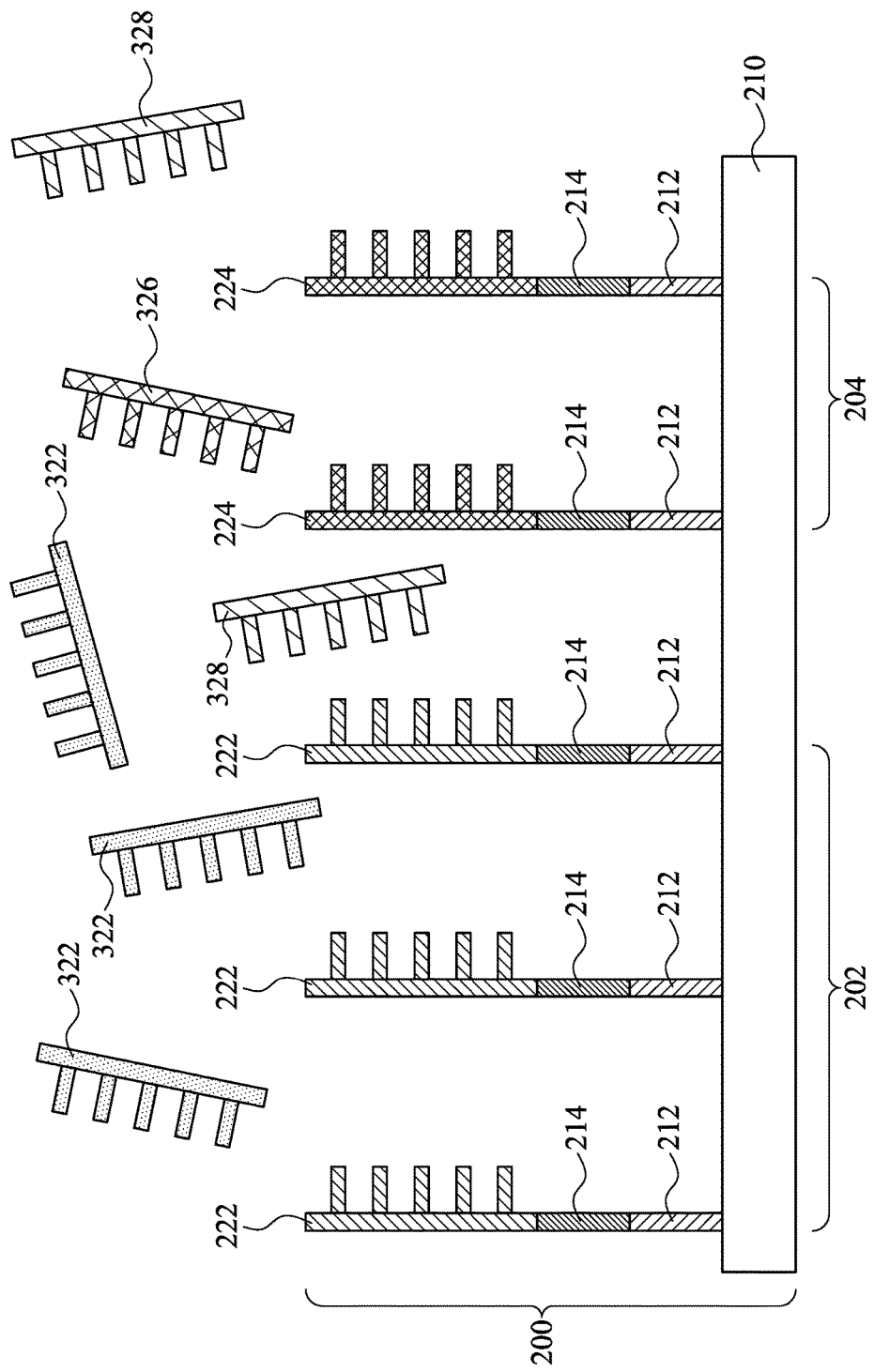

Reference is made to FIG. 3 and operation 1100 of FIG. 1, illustrating addition of a sample. The sample may include varied nucleic acid fragments. The nucleic acid fragments may be naturally occurring nucleotides and/or nucleotides that are not known to occur in nature. In some embodiments, the nucleic acid fragments are microRNA. In some embodiments, the sample includes first nucleic acid fragments 322, second nucleic acid fragments 326, and third nucleic acid fragments 328 as shown in FIG. 3. The first, second and third nucleic acid fragments 322, 326, and 328 may be the same or different type of nucleotides, and each type of the nucleic acid fragments has a sequence distinguishable from the other. That is, the first, second and third nucleic acid fragments 322, 326, and 328 are not identical. At least one or more bases are different therebetween.

Figure 4:
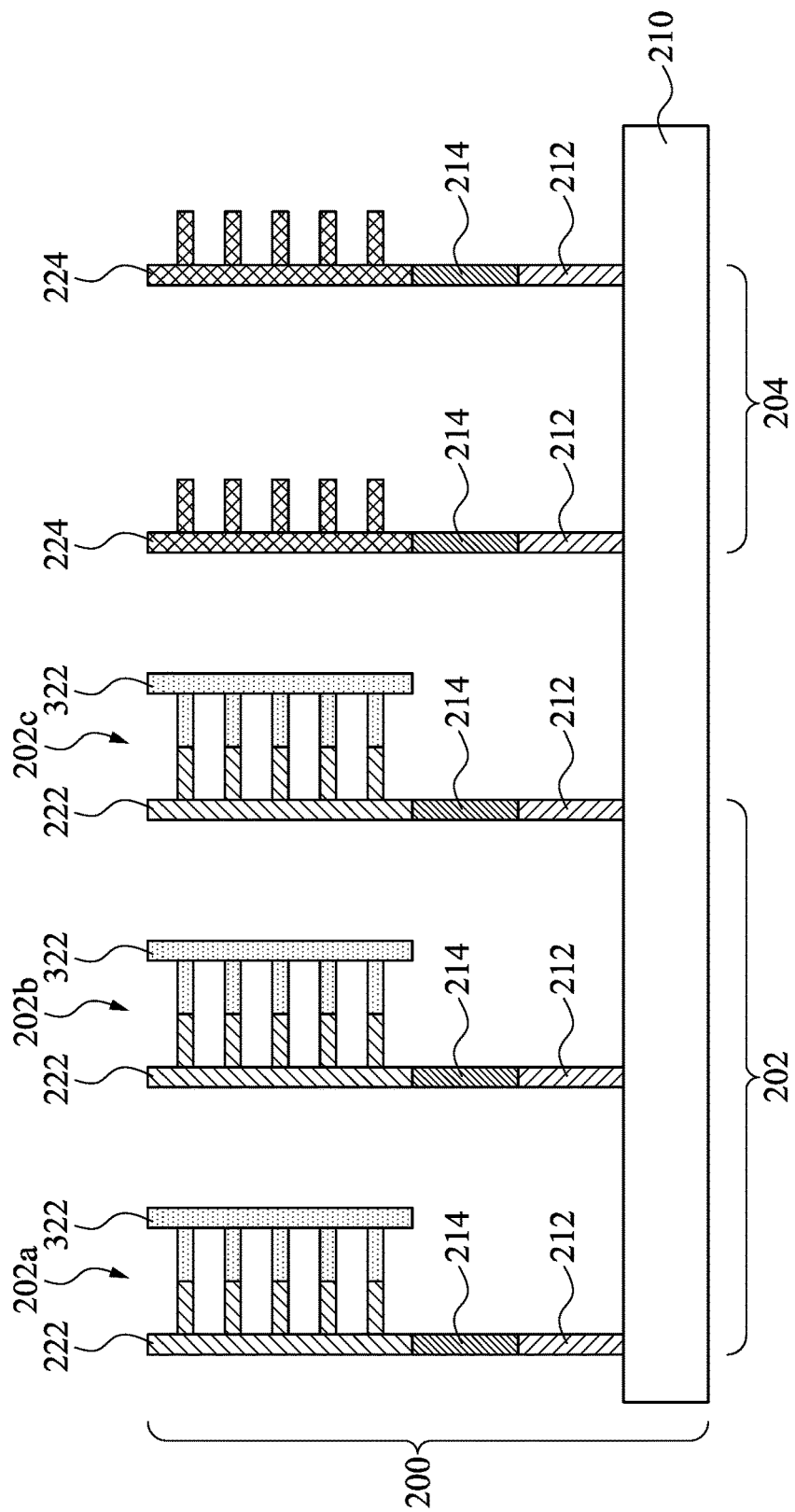

Reference is made to FIG. 4 and operation 1100 of FIG. 1, illustrating formation of hybridised double strands. The first oligonucleotide probes 202 and second oligonucleotide probes 204 each contains a complementary sequence to the sequence of interest. In some embodiments, as shown in FIG. 4, the first nucleic acid fragments 322 contain sequence of interest. This sequence of interest makes the first nucleic acid fragments 322 the target nucleic acid fragment. The sequence of interest may reflect a high risk of certain disorders or a key cellular function, for example. It should be understood that the first nucleic acid fragments 322 may have a sequence length longer than the sequence of interest. The first identification sequences 222 of the first oligonucleotide probes 202 capture the first nucleic acid fragments 322 because the first identification sequences 222 are complementary to the sequence of interest of the first nucleic acid fragments 322. While the second and third nucleic acid fragments 326 and 328 do not match the sequence of interest to either the first identification sequence 222 or the second identification sequence 224. The second and third nucleic acid fragments 326 and 328 will not be retained (i.e., unbound) by the oligonucleotide probes 200 and are washed away.

Reference is still made to FIG. 4. The binding between the first identification sequence 222 and the first nucleic acid fragments 322 makes a portion of the single stranded first oligonucleotide probes 202 into a hybridised double strand. The first nucleic acid fragments 322 are captured by the first identification sequences 222, and this combination results in hybridised double strands 202a, 202b, and 202c. The remaining portion of the first oligonucleotide probes 202, which includes the telomere sequence 214 and the immobilization anchor 212, is still in single strand state as shown in FIG. 4. The second oligonucleotide probes 204 do not capture nucleic acid fragment that contains sequence of interest complementary to the second identification sequences 224 and remain single stranded on the substrate 210 surface.

Figure 5:
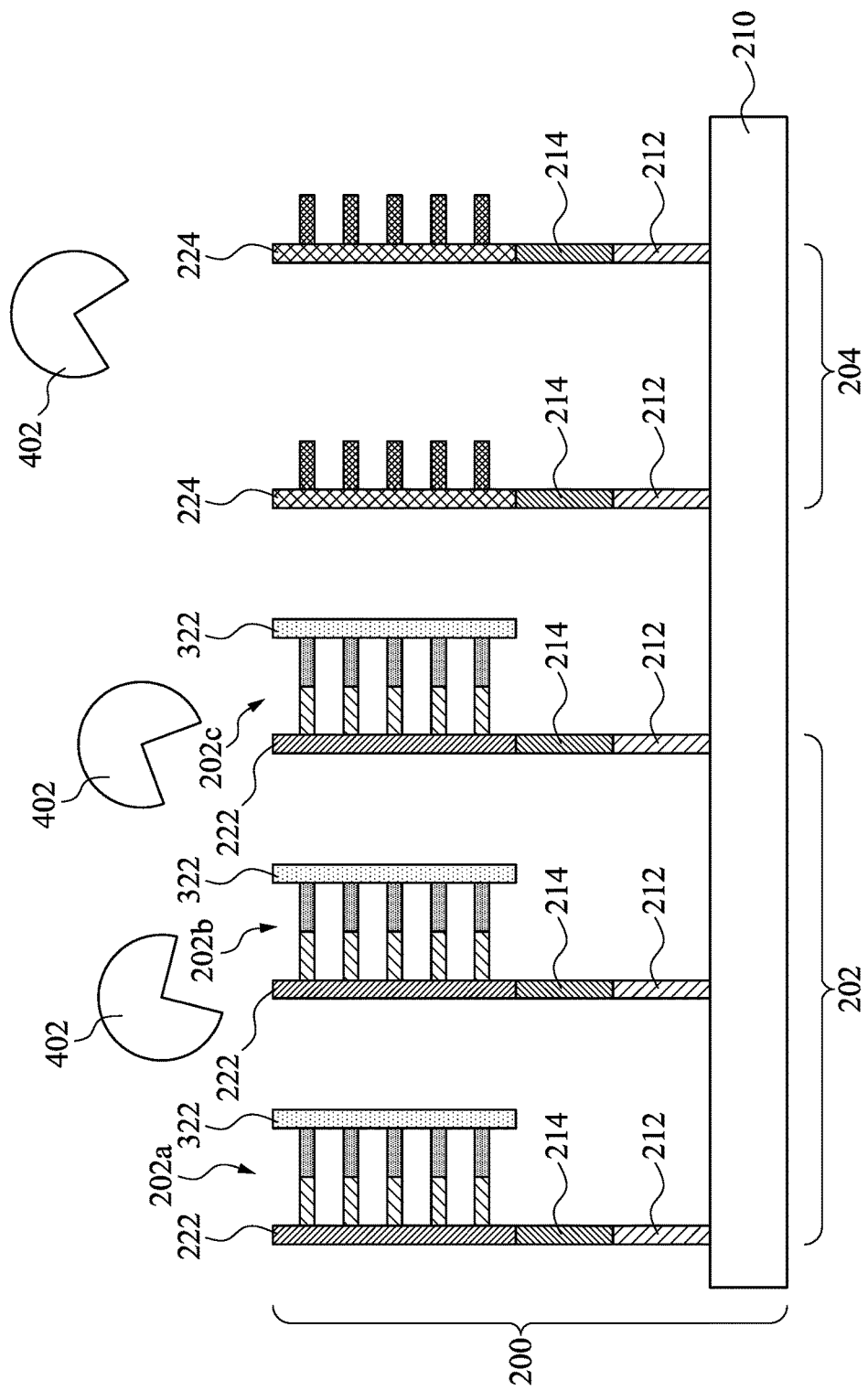

Reference is made to FIG. 5 and operation 1200 of FIG. 1, illustrating addition of duplex-specific nuclease (DSN). The substrate 210 has double stranded and single stranded fragments. The first identification sequences 222 and the first nucleic acid fragments 322 are hybridised double strands 202a, 202b, and 202c, while the second oligonucleotide probes 204 and the remaining portion of the first oligonucleotide probes 202 are single strands. The double-stranded state raises a flag to the duplex-specific nuclease 402, while the single-stranded segments do not attract attention from the duplex-specific nuclease 402.

Figure 6:
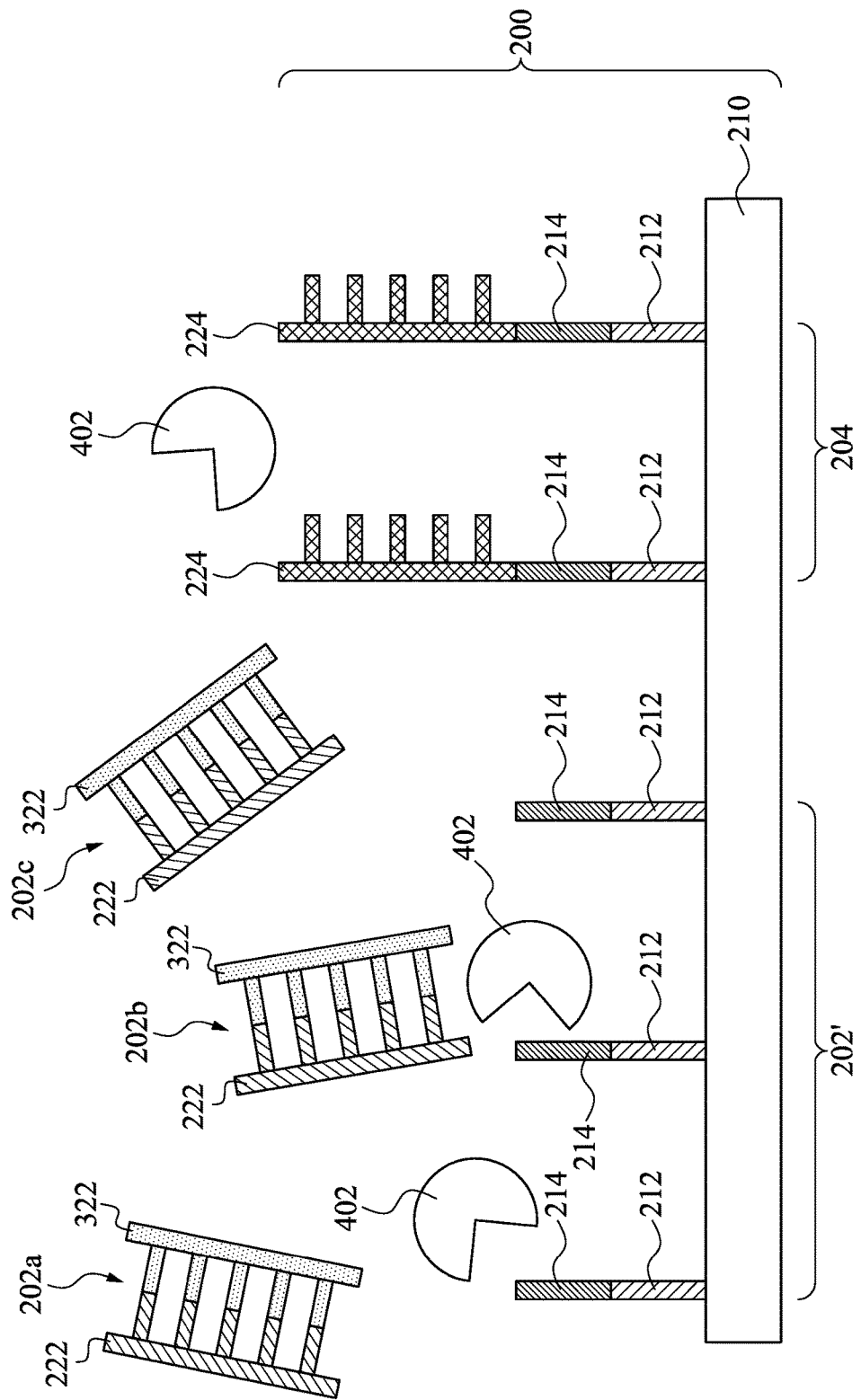

Reference is made to FIG. 6 and operation 1200 of FIG. 1, illustrating the cleavage of the double strands. The duplex-specific nuclease 402 recognizes the hybridised double strands 202a, 202b, and 202c and cuts the first identification sequences 222 and the first nucleic acid fragments 322 off from the first oligonucleotide probes 202. The second oligonucleotide probes 204 are intact because they are single strands that do not initiate duplex-specific nuclease 402 into action. The entire second oligonucleotide probes 204 stand on the substrate 210 surface, while only portions of the first oligonucleotide probes 202' remain. More specifically, the hybridised double strands 202a, 202b and 202c are cleaved, and the single stranded telomere sequences 214 and immobilization anchors 212 are left behind on the substrate 210 surface. The removal of the hybridised double strands 202a, 202b and 202c also results in exposure of the telomere sequences 214 of the first oligonucleotide probes 202'. The exposure of the telomere sequences 214 is translated into positive of sequence of interest. The second identification sequences 224 remain tagging along the telomere sequences 214 of the second oligonucleotide probes 204, such that the telomere sequences 214 of the second oligonucleotide probes 204 are not exposed. The exposure of the telomere sequence drives the subsequent reaction to take place.

Figure 7:
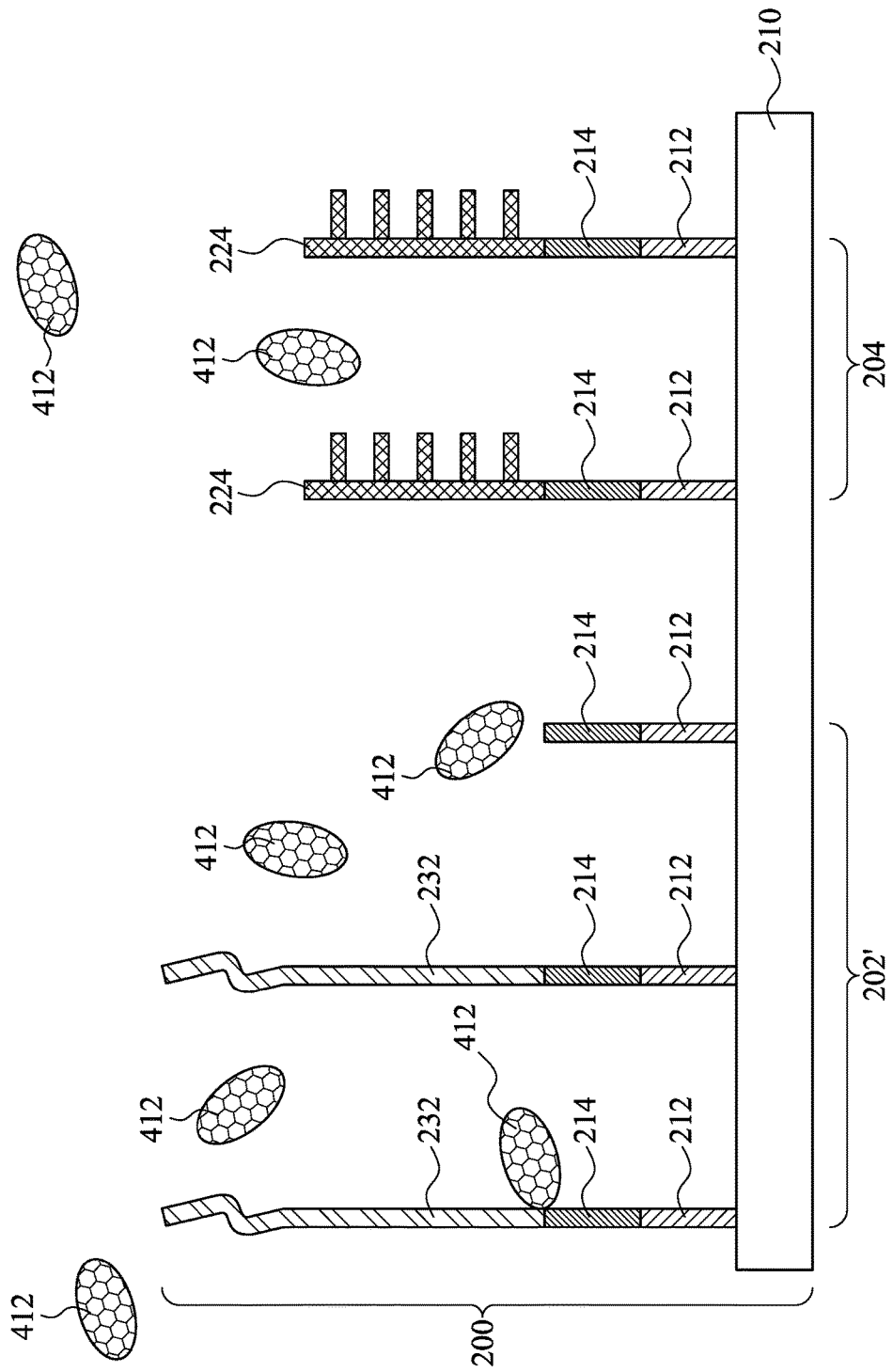

Reference is made to FIG. 7 and operation 1300 of FIG. 1, illustrating extension of telomere sequence. The hybridised double strands 202a, 202b, and 202c are removed, and the telomere sequences 214 are exposed. Telomerase, which is also known as terminal transferase, is a ribonucleoprotein that adds a species-dependent telomere repeat sequence to the 3' end of telomere sequence. The telomere repeat sequence has 6 bases in human, for example. When telomerase 412 are added into the reaction vessel, the exposed telomere sequences 214 of the first oligonucleotide probes 202' provide the binding sites for the telomerase 412. The telomere sequences 214 of the second oligonucleotide probes 204 are not exposed because the second identification sequences 224 are attached at the end. The telomerase 412 cannot find binding site on the second oligonucleotide probes 204 because the 3' end of telomere sequences 214 of the second identification sequences 224 are occupied. This discrimination allows telomerase 412 to produce telomere repeats at the exposed 3' end of the exposed telomere sequences 214 of the first oligonucleotide probes 202'. The telomere repeats 232 extend from the 3' end of the telomere sequences 214 of the first oligonucleotide probes 202 and may have thousands of the 6-base repeats.

In some embodiments, the presence of telomere repeats 232 indicates positive result of the existence of sequence of interest, while the second oligonucleotide probes 204 does not find complementary sequence of interest and remain negative (i.e., without the telomere repeat sequence). These positive and negative results are further visualized by the addition of detection probes 422.

Figure 8:
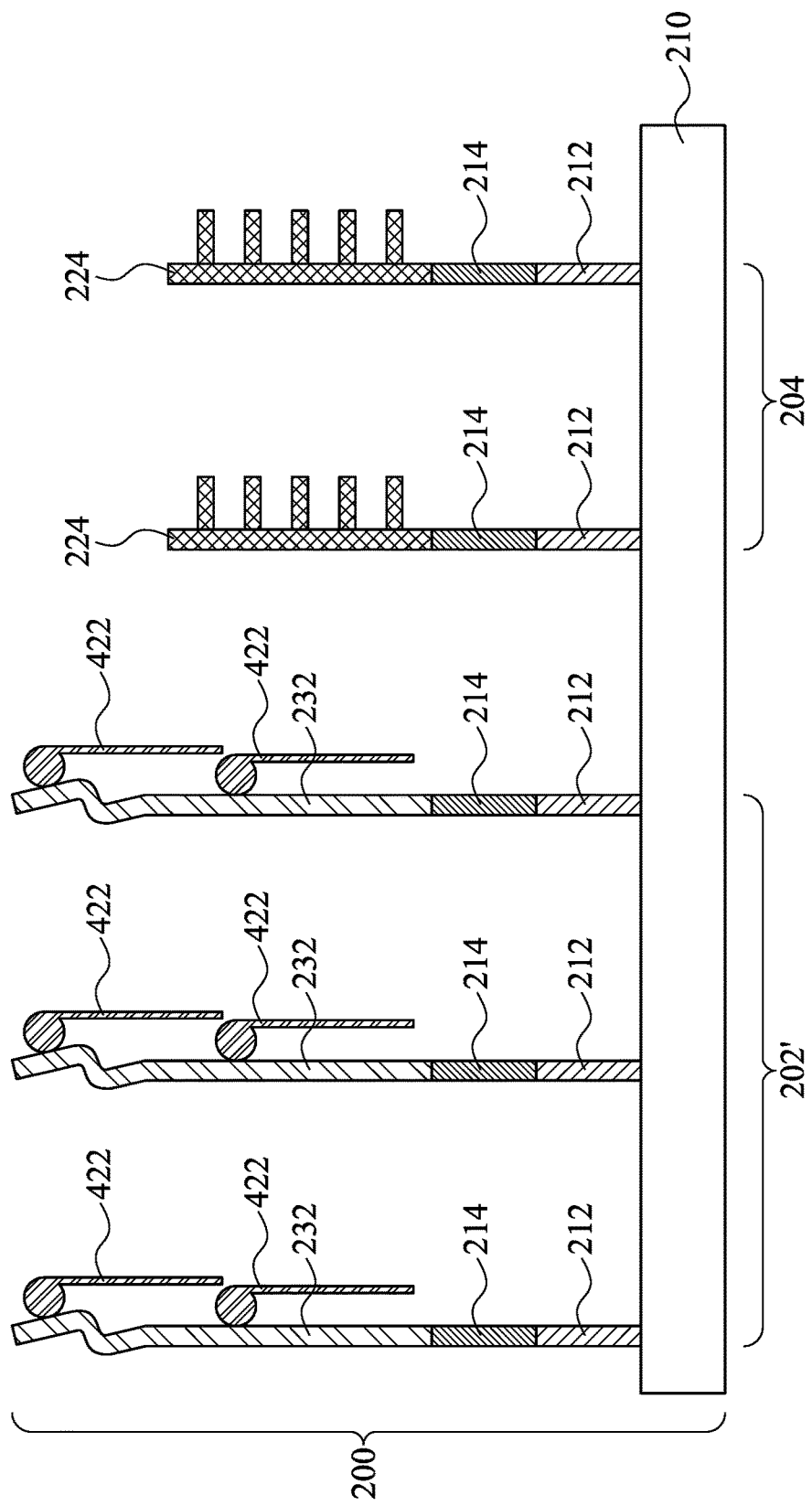

Reference is made to FIG. 8 and operation 1400 of FIG. 1, illustrating the addition and binding of the detection probes. The positive first oligonucleotide probes 202' are recognized by the detection probes 422 through the telomere or RAC repeats 232 and bind thereto. The binding of the detection probes to the said telomere or RAC repeats can be achieved by various means known in the art, comprising hybridization probes or ligation probes. The detection probes 422 may contain fluorescence signals that can be naked-eye visible under certain radiant wavelength. The detection probes 422 label the positive first oligonucleotide probes 202' and indicate the position of the cluster.

Figure 9:
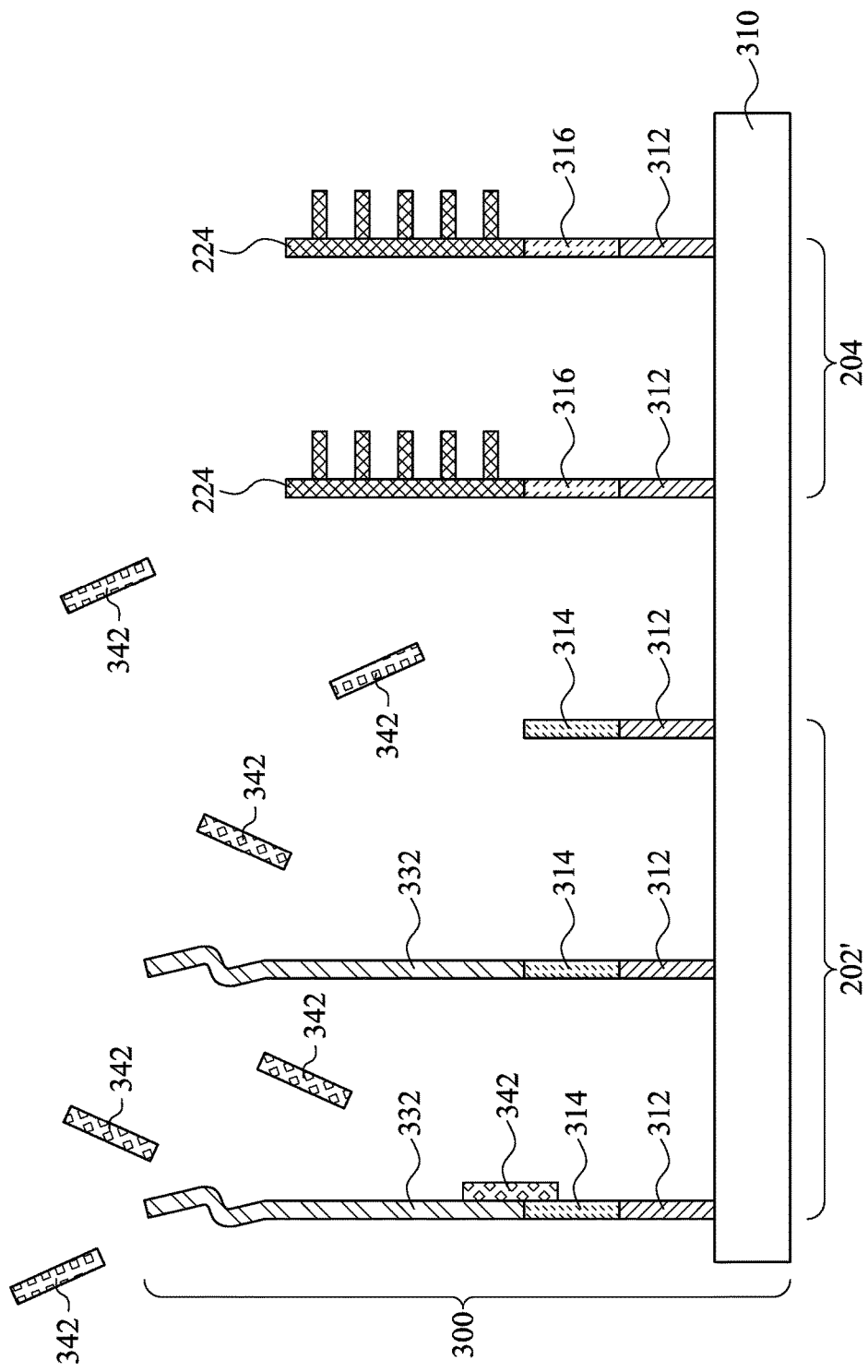

In some embodiments, the sequence of interest is visualized through rolling-circle amplification (RCA). Reference is made to FIG. 9 and operation 1300 of FIG. 1. Each of the probes 300 includes an immobilization anchor 312 and a primer sequence 314. The difference between the probes 200 and probes 300 arises from the reproducible sequences 214 and the primer sequences 314 and 316. Unlike the reproducible sequence 214, the primer sequences 314 and 316 include a specifically designed primer sequence that can be extended through RCA. For example, after cleavage of the double strands, the primer sequences 314 are exposed as shown in FIG. 6 and serves as a primer for further extension. As shown in FIG. 9, a circularized extension template 342 is then added to the sample and the RCA reaction is initiated. The added circularized extension template 342 includes a sequence that is complementary to the primer sequence 314 and has a unique sequence designed for target identification. The combination of the circularized extension template 342 and the primer sequence 314 results in repeats 332 on the substrate 310 and are identified by labelled detection probes as shown in FIG. 8. Again, the existence of repeats 332 of the circularized extension template 342 gives the positive indicator of the sequence of interest in the sample.

In some embodiments, the primer sequence 314 of the probe 300 may also contain a unique artificial nucleic acid sequence serving as an identification (ID) tag for the sequence of interest to be identified. Each of the ID tags is specific to the sequence of interest and can be identified in the subsequent detection steps. For example, as shown in FIG. 8, the primer sequences 314 and 316 contains different types of identification tags to their sequences of interest respectively. The method of identification and quantitation of the said ID tags are well known in the art, comprising probe hybridization, ligation and sequencing. The use of ID tags on the primer sequences 314 and 316 on the probes 300 enables simultaneous analysis of multiple sequences of interest.

Figure 10:
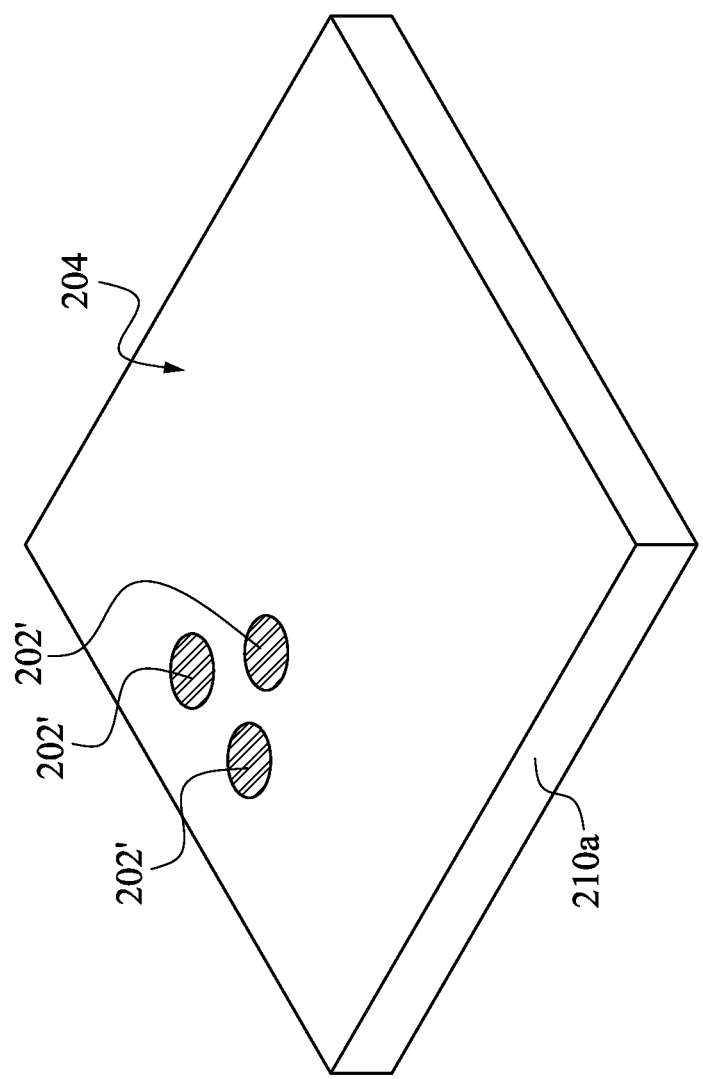
FIG. 10 illustrate a cartridge for receiving samples in a method of nucleic acid fragment in accordance with some embodiments of the instant disclosure.

Reference is made to FIG. 10, illustrating a perspective view of a substrate in accordance with some embodiments of the instant disclosure. The positive first oligonucleotide probes 202' are visualized by the detection probes 422 on the substrate 210a, while the negative second oligonucleotide probes 204 cannot be seen on the substrate 210a because the negative second oligonucleotide probes 204 do not bind with the detection probes 422. Different types of oligonucleotide probes are grouped together on the substrate 210a such that the positive result is accompanied with a spatial resolution. It should be understood that the immobilization anchors 212 and reproducible sequences 214 are identical to each of the oligonucleotide probes 200. If there are four different types of oligonucleotide probes (i.e., four different sequences of interest), these four different types of oligonucleotide probes will be arranged in four clusters on the substrate 210a. When the sequence of interest is present in a sample, the positive oligonucleotide probes will be visualized by the detection probes. By identifying the position of these positive oligonucleotide probes on the substrate 210a, the sequence of interest can be determined.

Figure 11:
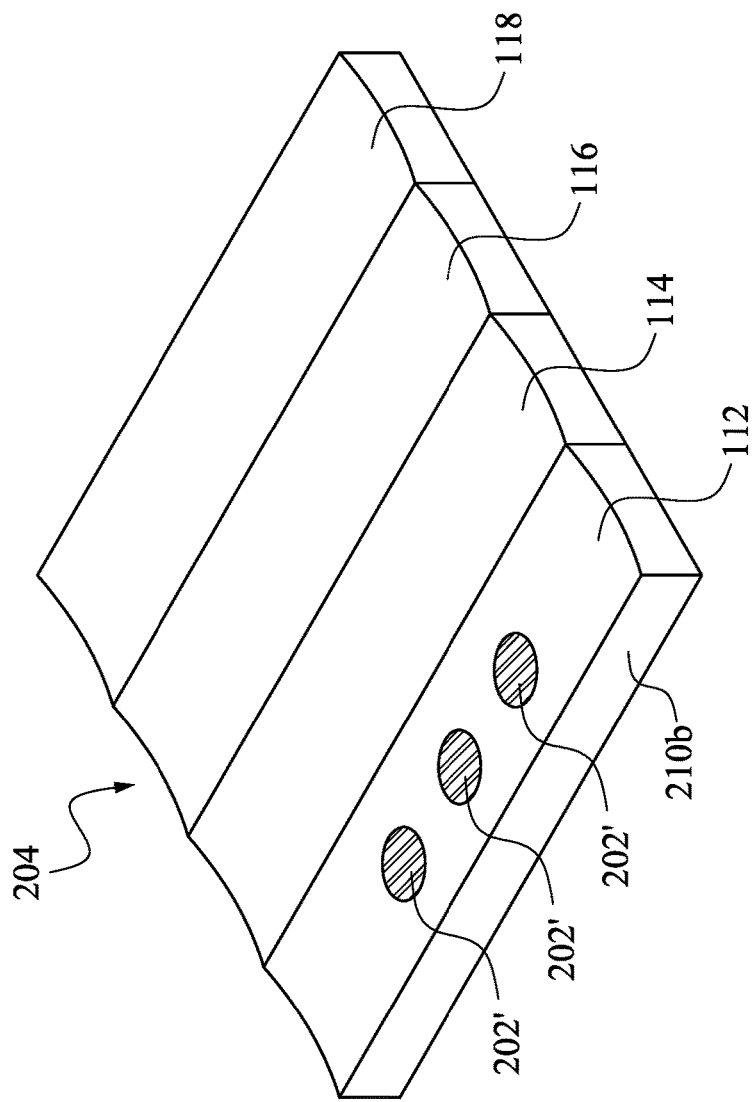
FIG. 11 illustrate a substrate for receiving samples in a method of nucleic acid fragment detection in accordance with some embodiments of the instant disclosure.

Reference is made to FIG. 11, illustrating a perspective view of a substrate in accordance with some embodiments of the instant disclosure. The substrate 210b is different from the substrate 210a due to the cartridge design. In some embodiments, the substrate 210b has four cartridges 112, 114, 116, and 118. The cartridges 112, 114, 116, and 118 are shallow depressions that are parallel to each other in a longitudinal direction on the substrate 210b. Each of the cartridges 112, 114, 116, and 118 contains a different type of oligonucleotide probe. The spatial resolution of the nucleic acid fragment detection is defined by the channels. For example, as shown in FIG. 11, the first oligonucleotide probes 202 are disposed in the cartridge 112 and the second oligonucleotide probes 204 are disposed in the cartridge 114. In some embodiments, the second oligonucleotide probes 204 may be disposed in the cartridge 116 or 118. After the positive oligonucleotide probes are visualized, the cartridge 112 shows the signal from the detection probes 422. This information is translated into that the sequence of interest of the first oligonucleotide probes 202 is present in the sample, while the sequence of interest of the second oligonucleotide probes 204 are not. The spatial resolution arises from the lanes of cartridges 112, 114, 116, and 118.

In some embodiments, oligonucleotide probes 300 have different ID tags that are used for simultaneous analysis of multiple sequences of interest in the biological sample. Each of the ID tags is assigned as an identifier for a specific target sequence. In some embodiments, the oligonucleotide probes 300 having different ID tags do not be spatially isolated from each other on the substrate 310. In some embodiments, the oligonucleotide probes 300 having different ID tags are spatially isolated from each other on the substrate 310.

In some embodiments, the substrate 210 may be used as a quantitation tool for the target nucleic acid fragments in a sample. More specifically, the substrate 210 includes a plurality of wells and the total number of wells on the substrate is known by design. In addition each of the wells contains oligonucleotide probes 200 of the same sequence. A sample solution containing the target nucleic acid fragments of interest is randomly distributed among the wells on the substrate, with less than one copy of target nucleic acid fragment of interest in each well on average. Every positive well represents one strand of sequence of interest in the sample. The quantitation results can be obtained through Poisson statistical analysis of all positive and negative wells, similar to digital PCR analysis. This nucleic acid fragment detection method may be seen as a digital counting method of target of interest.

FIGS. 12 through 17 illustrate various stages of a nucleic acid fragment detection method in accordance with some embodiments of the instant disclosure.

Figure 12:
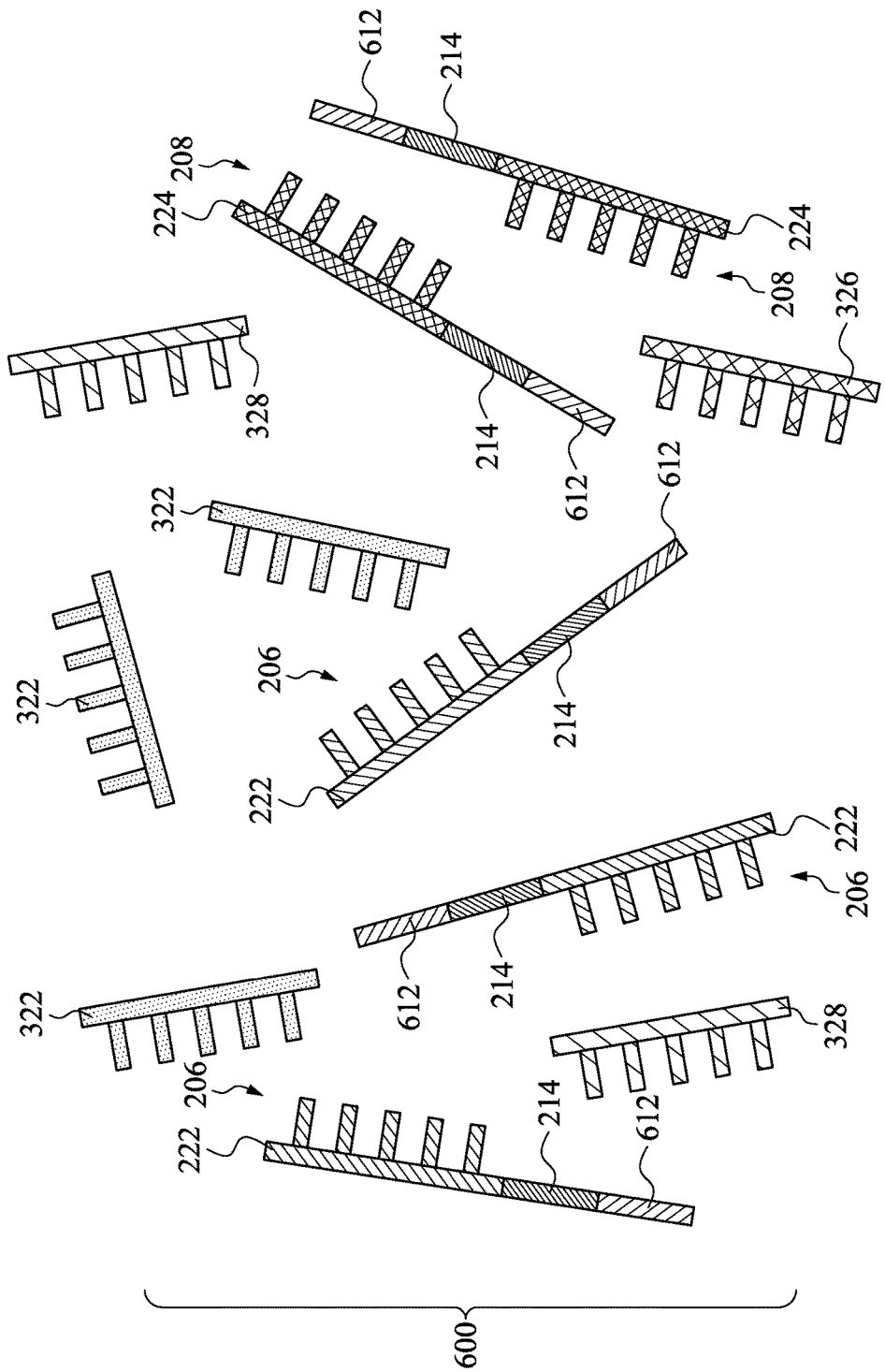
FIGS. 12 through 17 illustrate a method of nucleic acid fragment detection at various stages in accordance with some embodiments of the instant disclosure.

Reference is made to FIG. 12, illustrating a plurality of oligonucleotide probes 600. The difference between the oligonucleotide probes 600 and the oligonucleotide probes 200 arises from the anchor portion. The oligonucleotide probes 200 have immobilization anchors 212, while the oligonucleotide probes 600 are not fixed on a substrate. Each of the oligonucleotide probes 600 has an anchor 612. The anchor 612 will not settle until a later stage in the nucleic acid fragment detection process. As a result, the oligonucleotide probes 600 float in the solution. The first oligonucleotide probes are designated as 206, and the second oligonucleotide probes are designated as 208. The oligonucleotide probes 200 and 600 have substantially the same structure, but the oligonucleotide probes 600 have anchors 612 instead of immobilization anchors 212.

Reference is made to FIG. 12 and operation 1100 of FIG. 1, illustrating addition of a sample. In some embodiments, the sample includes first nucleic acid fragments 322, second nucleic acid fragments 326, and third nucleic acid fragments 328 as shown in FIG. 12.

Figure 13:
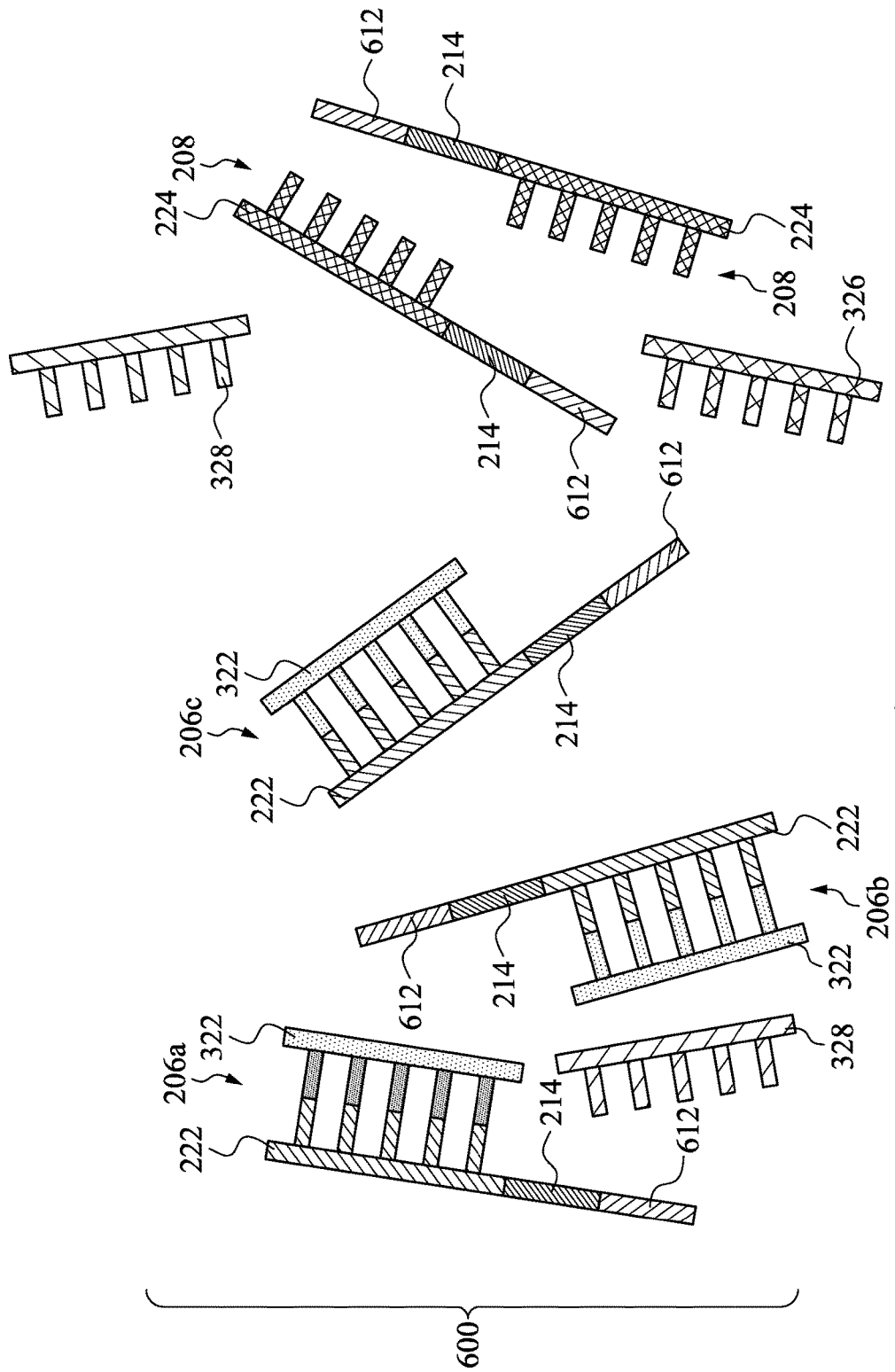

Reference is made to FIG. 13 and operation 1100 of FIG. 1, illustrating formation of hybridised double strands. The first oligonucleotide probes 206 and second oligonucleotide probes 208 each contains a complementary sequence to the sequence of interest. In some embodiments, as shown in FIG. 13, the first nucleic acid fragments 322 contain sequence of interest. This sequence of interest makes the first nucleic acid fragments 322 the target nucleic acid fragment. The first identification sequences 222 of the first oligonucleotide probes 206 capture the first nucleic acid fragments 322, while the second and third nucleic acid fragments 326 and 328 do not match the sequence of interest to either the first identification sequence 222 or the second identification sequence 224. The second and third nucleic acid fragments 326 and 328 will not be retained by the oligonucleotide probes 200 and are washed away. The binding between the first identification sequence 222 and the first nucleic acid fragments 322 makes a portion of the single stranded first oligonucleotide probes 206 into a hybridised double strand.

Figure 14:
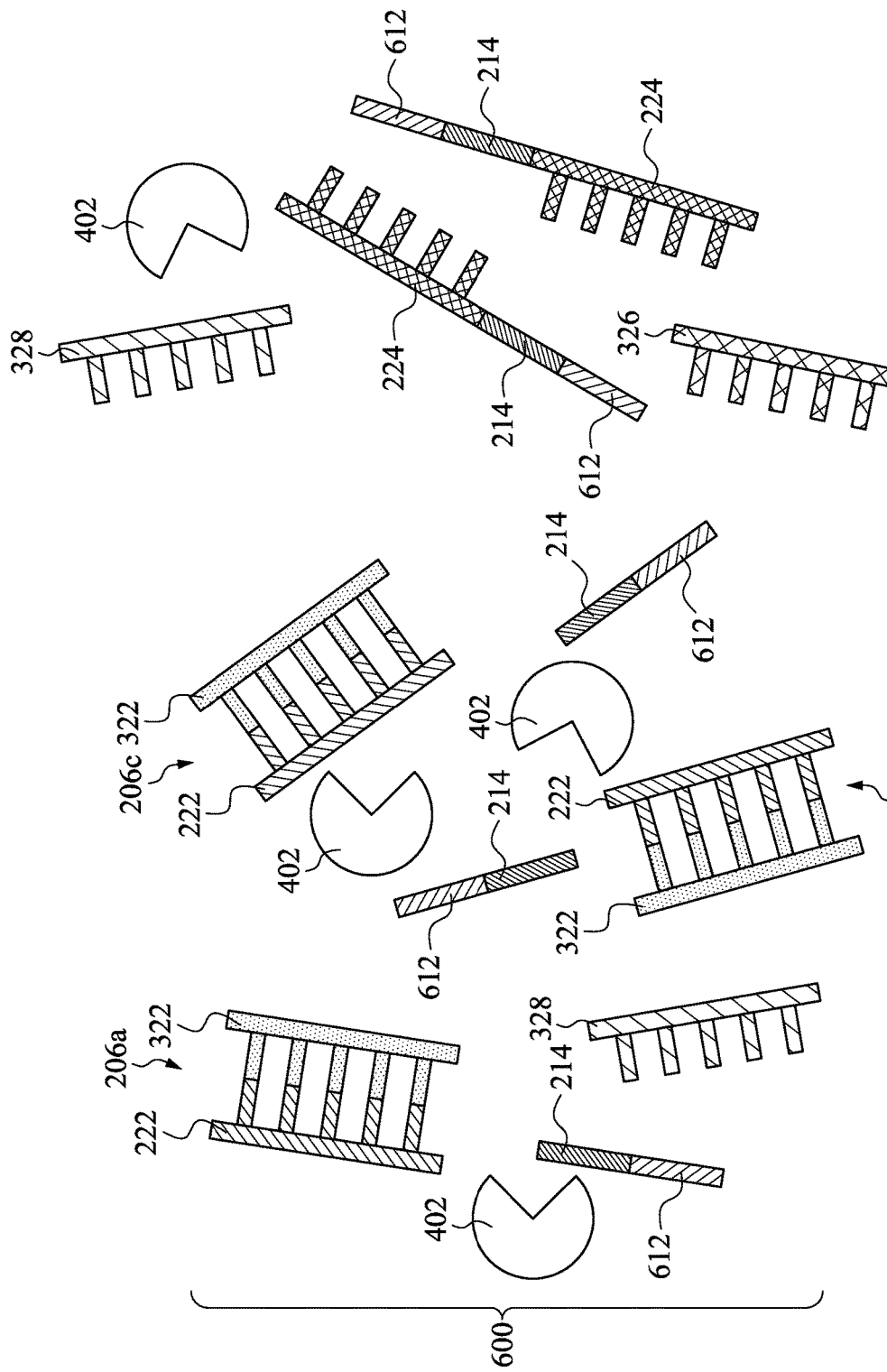

Reference is made to FIG. 14 and operation 1200 of FIG. 1, illustrating addition of duplex-specific nuclease (DSN). The first identification sequences 222 and the first nucleic acid fragments 322 are hybridised double strands 206a, 206b, and 206c, while the second oligonucleotide probes 208 and the remaining portion of the first oligonucleotide probes 206 are single strands. The double-stranded state raises a flag to the duplex-specific nuclease 402, while the single-stranded segments do not attract attention from the duplex-specific nuclease 402.

Reference is made to FIG. 14, illustrating the cleavage of the double strands. The duplex-specific nuclease 402 recognizes the hybridised double strands 206a, 206b, and 206c and cuts the first identification sequences 222 and the first nucleic acid fragments 322 off from the first oligonucleotide probes 206. The second oligonucleotide probes 208 are intact because they are single strands that do not initiate duplex-specific nuclease 402 into action. The removal of the hybridised double strands 206a, 206b and 206c results in exposure of the 3' end of telomere sequences 214 of the first oligonucleotide probes 206'. The exposure of the 3' end of telomere sequences 214 is translated into positive of sequence of interest. The exposure of the telomere sequence drives the subsequent reaction to take place.

Figure 15:
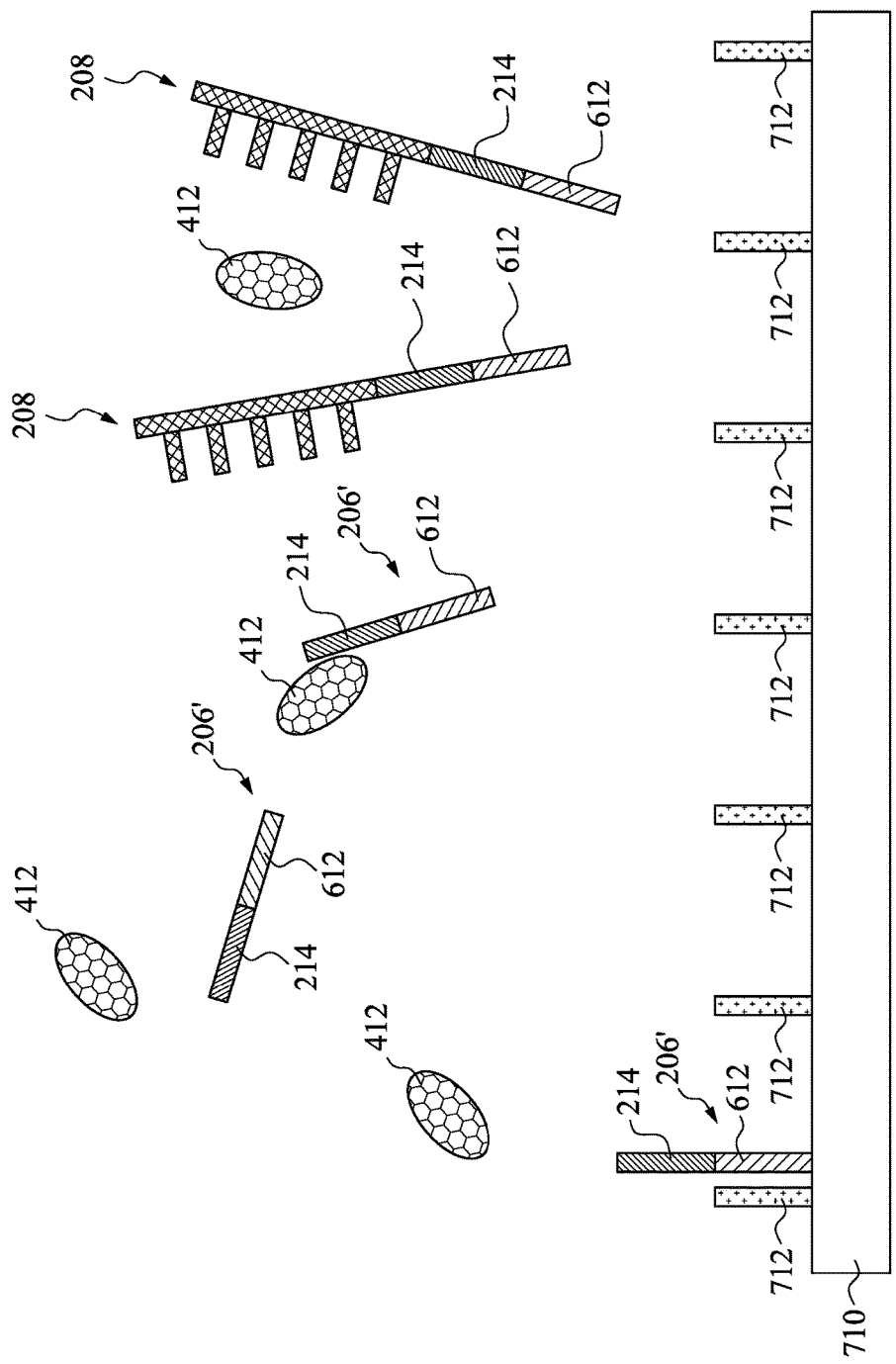

Reference is made to FIG. 15, illustrating anchoring of oligonucleotide probes and addition of telomere sequence. A substrate 710 is provided. The substrate 710 has a plurality of anchor sites 712. In some embodiments, different anchors on the substrate can be used for different sequences of interest in order to incorporate spatial separation for each sequence of interest. The anchor sites 712 contain complementary sequence to the anchors 612 so as to immobilize the floating oligonucleotide probes 600. The oligonucleotide probes 600 recognize the anchor sites 712 through the anchors 612 and bind to the anchor sites 712 on the substrate 710.

Figure 16:
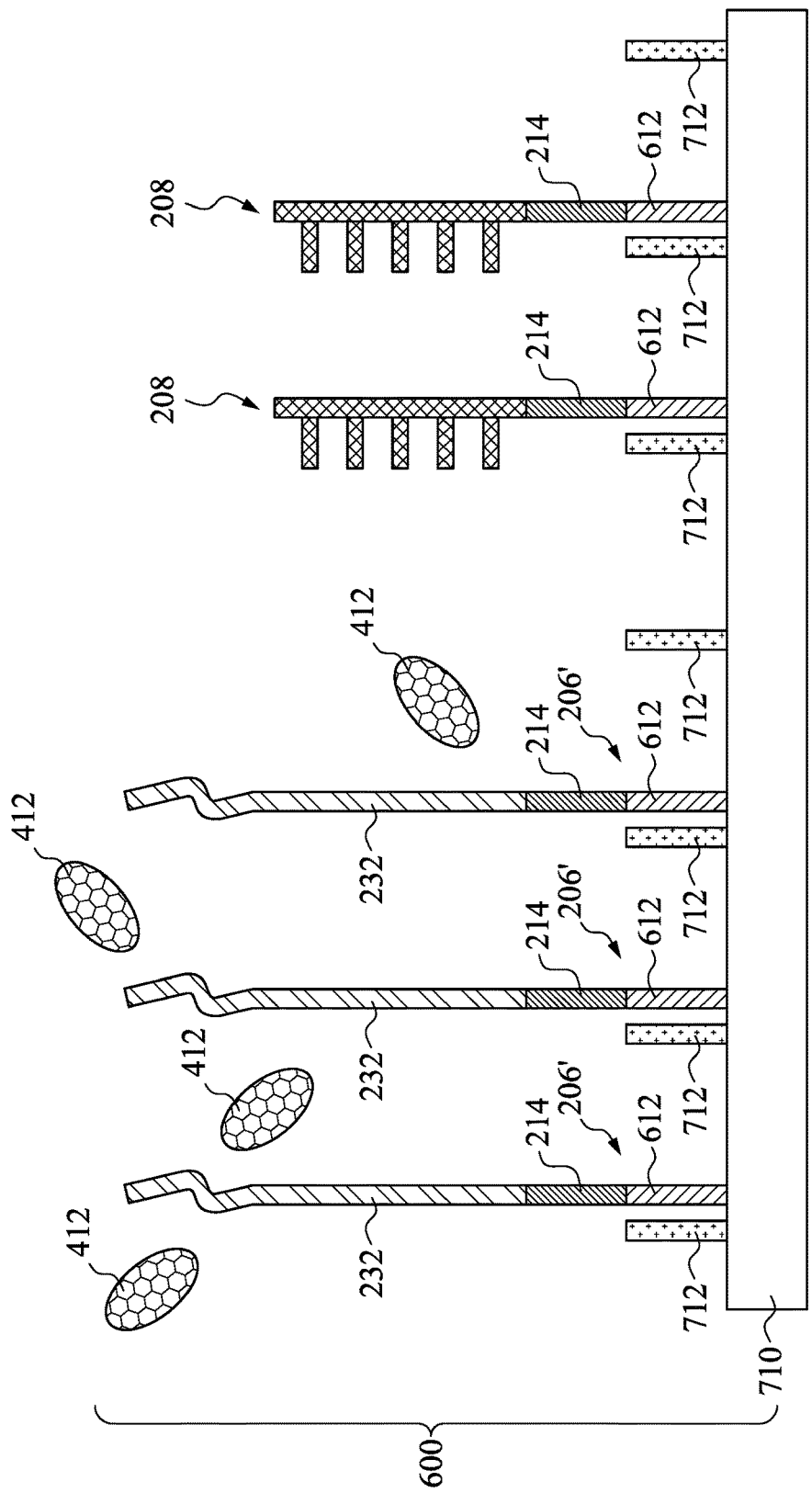

Reference is made to FIG. 16, illustrating extension of telomere sequence. After the hybridised double strands 206a, 206b, and 206c are removed, and the 3' end of the telomere sequences 214 are exposed. When telomerase 412 are added into the reaction vessel, the exposed telomere sequences 214 of the first oligonucleotide probes 206' provide the binding sites for the telomerase 412. The telomere sequences 214 of the second oligonucleotide probes 208 are not exposed because the second identification sequences 224 are attached at the end. The telomere repeats 232 extend from the 3' end of the telomere sequences 214 of the first oligonucleotide probes 206 and may have thousands of the 6-base repeats but take no action to the second oligonucleotide probes 208.

Figure 17:
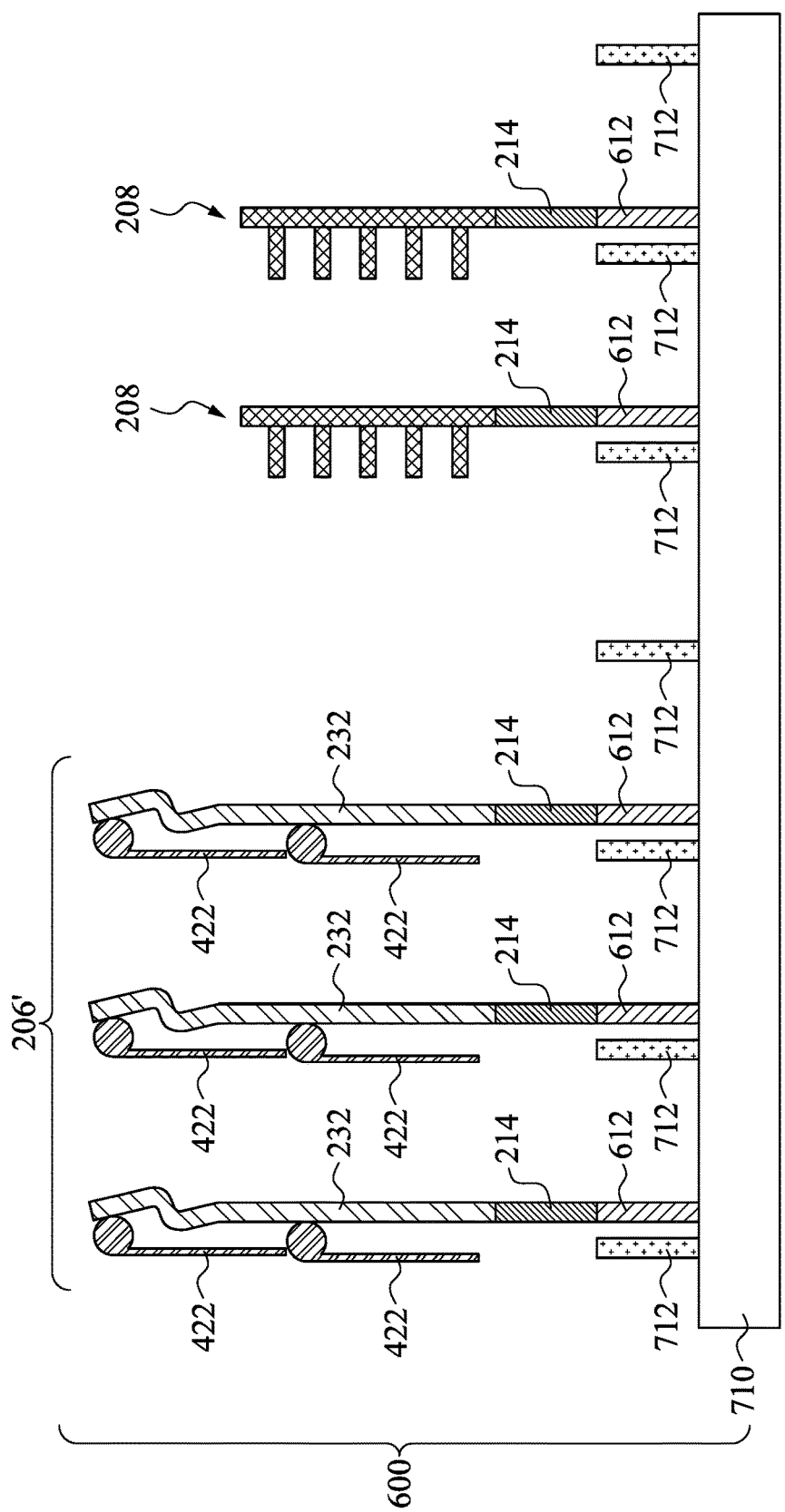

These positive and negative results are further visualized by the addition of detection probes 422. Reference is made to FIG. 17, illustrating the addition and binding of the detection probes 422. The positive first oligonucleotide probes 206' are recognized by the detection probes 422 through the telomere repeats 232 and bind thereto. The detection probes 422 may contain fluorescence signals that can be naked-eye visible under certain radiant wavelength. The detection probes 422 label the positive first oligonucleotide probes 206' and indicate the position of the cluster. The positive identification of telomere repeats 232 indicate positive result of the existence of sequence of interest, while the second oligonucleotide probes 208 does not find complementary sequence of interest and remain negative (i.e., without the telomere repeat sequence).

In summary, the disclosed invention provides a method for the identification and quantitation of miRNA fragments in a biological sample. The oligonucleotide probe uses identification sequence to capture sequence of interest and forms into double-stranded nucleic acid fragment. The double strand is then cleaved by duplex-specific nuclease and the 3' end of the reproducible sequence of the oligonucleotide probe will be exposed. The exposure of the reproducible sequence indicates a positive result of the sequence of interest. Subsequently, the positive oligonucleotide probes are visualized by detection probes.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method of nucleic acid fragment detection, the method comprising:
    capturing a target nucleic acid fragment by an oligonucleotide probe to form a section of hybridised double strand, the oligonucleotide probe having an identification sequence and a reproducible sequence, the identification sequence being complementary to the target nucleic acid fragment;
    removing the hybridised double strand section to expose the reproducible sequence of the oligonucleotide probe, wherein the removing the hybridised double strand comprises: cleaving the hybridized double strand off the oligonucleotide probe by duplex specific nuclease (DSN);
    producing repeats of the reproducible sequence; and
    labelling the repeats of the reproducible sequence by a detection probe.

2. The method of claim 1, wherein the production of repeats of the reproducible sequence comprises:
    adding telomerase.

3. The method of claim 1, wherein the production of repeats of the said reproducible sequence comprises:
    adding circularized extension template that comprises a sequence complementary to the reproducible sequence.

4. The method of claim 1, wherein the detection probe comprises a signal label that generates detectable signals, including fluorescence signals, electrochemical signals, or chemiluminescence signals.

5. The method of claim 1, wherein the oligonucleotide probe is fixed on a substrate.

6. The method of claim 5, further comprising:
    identifying the target nucleic acid fragment according to a spatial resolution.

7. The method of claim 1, further comprising using a substrate having a plurality of wells, and each of the wells having a plurality of said oligonucleotide probe.

8. The method of claim 7, further comprising:
    quantifying a number of the target nucleic acid fragment by counting a number of wells having the presence of the said detection probe.

9. The method of claim 1, further comprising:
    providing a substrate having an immobile probe; and
    capturing the repeats of the reproducible sequence through the immobile probe, wherein the immobile probe having a sequence complementary to a segment of the oligonucleotide probe.

10. The method of claim 1, further comprising:
    removing unbound nucleic acid fragment.

11. The method of claim 1, wherein the target nucleic acid fragment comprises micro ribonucleic acid (miRNA).

12. The method of claim 1, wherein the oligonucleotide probe comprises deoxyribonucleic acid (DNA).

13. The method of claim 1, wherein the reproducible sequence of the oligonucleotide probe comprises an identification tag specific to the target nucleic acid fragment.

14. The method of claim 1, wherein the oligonucleotide probe is fixed on a substrate, the substrate has a plurality of wells, a number of copies of the target nucleic acid fragment is plural, and on average less than one copy of the target nucleic acid fragment is in each of the wells.

* * * * *